(12) United States Patent
Gilbert

(10) Patent No.: US 9,186,202 B2
(45) Date of Patent: *Nov. 17, 2015

(54) ELECTROSURGICAL GENERATOR

(71) Applicant: COVIDIEN LP, Mansfield, MA (US)

(72) Inventor: James A. Gilbert, Boulder, CO (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/341,279

(22) Filed: Jul. 25, 2014

(65) Prior Publication Data

US 2014/0336633 A1    Nov. 13, 2014

Related U.S. Application Data

(63) Continuation of application No. 12/549,563, filed on Aug. 28, 2009, now Pat. No. 8,790,335.

(51) Int. Cl.
*A61B 18/18*        (2006.01)
*A61B 18/12*        (2006.01)
(Continued)

(52) U.S. Cl.
CPC ......... *A61B 18/1206* (2013.01); *A61B 18/1233* (2013.01); *A61B 18/14* (2013.01); *A61B 18/1442* (2013.01); *A61B 18/1477* (2013.01); *A61B 2018/00827* (2013.01); *A61B 2018/00892* (2013.01); *A61B 2018/1425* (2013.01)

(58) Field of Classification Search
CPC ........... A61B 18/1206; A61B 18/1233; A61B 18/14; A61B 18/1442; A61B 18/1477; A61B 2018/00827; A61B 2018/00892; A61B 2018/1425

USPC ...................................................... 606/32–35
See application file for complete search history.

(56) References Cited

U.S. PATENT DOCUMENTS 4,630,218 A    12/1986    Hurley
4,969,885 A    11/1990    Farin
(Continued)

FOREIGN PATENT DOCUMENTS

DE          179607 C     3/1905
DE          390937 C     3/1924
(Continued)

OTHER PUBLICATIONS

U.S. Appl. No. 10/406,690, filed Apr. 3, 2003.
(Continued)

*Primary Examiner* — Joseph Stoklosa
*Assistant Examiner* — Amanda Zink

(57)    ABSTRACT

An electrosurgical system is provided. The electrosurgical system includes an electrosurgical generator adapted to supply electrosurgical energy to tissue. A power source operably couples to the electrosurgical generator and is configured to deliver power to one or more types of loads connected to the electrosurgical generator. The electrosurgical generator includes a controller including a microprocessor coupled to the electrosurgical generator and configured to control the output of the electrosurgical generator. A fiber optic connection circuit is in operative communication with the controller and includes one or more types of logic devices and one or more types of fiber optic channels. The fiber optic connection circuit is configured to mitigate leakage current associated with at least one of a plurality of components operatively associated with the electrosurgical generator by providing isolation.

12 Claims, 3 Drawing Sheets

(51) Int. Cl.
  *A61B 18/14* (2006.01)
  *A61B 18/00* (2006.01)

(56) References Cited

U.S. PATENT DOCUMENTS

| | | | |
|---|---|---|---|
| 5,157,603 | A | 10/1992 | Scheller et al. |
| 5,432,459 | A | 7/1995 | Thompson et al. |
| 5,436,566 | A | 7/1995 | Thompson et al. |
| 5,681,307 | A | 10/1997 | McMahan |
| 6,288,604 | B1 * | 9/2001 | Shih et al. .................. 330/9 |
| 6,733,495 | B1 | 5/2004 | Bek et al. |
| 6,749,624 | B2 | 6/2004 | Knowlton |
| 7,118,564 | B2 | 10/2006 | Ritchie et al. |
| 7,164,277 | B2 | 1/2007 | Nishimura et al. |
| 8,790,335 | B2 | 7/2014 | Gilbert |
| 2002/0121910 | A1 | 9/2002 | Rome et al. |
| 2004/0030328 | A1 * | 2/2004 | Eggers et al. ................ 606/34 |
| 2006/0232283 | A1 | 10/2006 | Nishimura et al. |
| 2008/0281311 | A1 * | 11/2008 | Dunning et al. ............. 606/32 |
| 2010/0049187 | A1 * | 2/2010 | Carlton et al. ............... 606/34 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4339049 A1 | 5/1995 |
| DE | 19717411 A1 | 11/1998 |
| DE | 19848540 A1 | 5/2000 |
| EP | 0 246 350 A1 | 11/1987 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 1051948 A2 | 11/2000 |
| EP | 1810631 A2 | 7/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 2006/050888 A1 | 5/2006 |

OTHER PUBLICATIONS

U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.
U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.
U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.

(56) References Cited

OTHER PUBLICATIONS

Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.
International Search Report EP10174476 dated Nov. 12, 2010.

\* cited by examiner

ELECTROSURGICAL GENERATOR

CROSS REFERENCE TO RELATED APPLICATIONS

The present application is a continuation of U.S. patent application Ser. No. 12/549,563, filed on Aug. 28, 2009, the entire contents of which are incorporated by reference herein.

BACKGROUND

1. Technical Field

The present disclosure relates to an electrosurgical generator and, more particularly, to an electrosurgical generator including a fiber optic correction circuit configured to mitigate high and low frequency leakage currents associated with the electrosurgical generator.

2. Description of Related Art

Electrosurgical generators, e.g., radio frequency electrosurgical generators, configured for use in performing an electrosurgical procedure are well known in the art. Leakage currents, inadvertent currents between an electronic device and earth ground, are a serious concern in RF devices such as an RF electrosurgical generator/electrode system. Leakage currents may be attributed to low frequency leakage currents, which may be associated with the power source, patient leads and/or one or more outputs. Leakage current may also be attributed to high frequency leakage currents, such as, for example, bipolar leakage current and/or monopolar leakage current, each of which may be present at an energy platform terminal associated with an RF electrosurgical generator.

Methods for reducing and/or mitigating leakage currents are known in the art. More particularly, a method for mitigating leakage currents may include providing one or more isolation barriers in the form of an electrostatic shield at an RF output module of an electrosurgical generator. The RF output module may also include two transformers coupled together to form a coupling circuit that acts as an electrostatic shield. In this instance, a relay switch may be operatively connected to the RF output module and connected to a second output and/or load. The relay may include a contact shield enclosed in an earth potential shield associated with the RF electrosurgical generator.

Another method may include isolating the above relay by adding an opto-isolated barrier energized by one or more floating power supplies to the relay, which effectively places the relay on a patient side of the RF electrosurgical generator and eliminates the need for electrostatic shielding at the RF output module.

The disadvantages of the above-methods may include cost, transformer and/or relay efficiencies, size, and so on. In addition, in the instance where the coupling circuit is used as an electrostatic shield, the shield's own voltage represents an effective opening in the shield. This effective opening may cause unwanted electrical effects to neighboring electrical circuits, which, as can be appreciated by one skilled in the art, may cause the RF electrosurgical generator to function in a manner unintended by a user and/or manufacturer.

SUMMARY

The present disclosure provides an electrosurgical system. The electrosurgical system includes an electrosurgical generator adapted to supply electrosurgical energy to tissue. A power source operably couples to the electrosurgical generator and is configured to deliver power to one or more types of loads connected to the electrosurgical generator. The electrosurgical generator includes a controller including a microprocessor coupled to the electrosurgical generator and configured to control the output of the electrosurgical generator. A fiber optic connection circuit is in operative communication with the controller and includes one or more types of logic devices and one or more types of fiber optic channels. The fiber optic connection circuit is configured to mitigate leakage current associated with at least one of a plurality of components operatively associated with the electrosurgical generator by providing isolation.

In embodiments, the one or more types of logic devices is selected from the group consisting of a complex programmable logic device and a field programmable gate array.

In embodiments, the one or more types of fiber optic channels is based on a data link protocol selected from the group consisting of at least Ethernet, R5232/422/485, and S/PDIF.

In embodiments, the plurality of components associated with the generator includes one of a button and slider control; one of a port selection and relay control; and one of a voltage and current sensor.

In embodiments, the fiber optic connection circuit further includes one or more buffers operatively disposed between the controller and the logic device.

In embodiments, each of the voltage and current sensors is connected to an RF output module of the generator.

In embodiments, the controller is operatively disposed within the electrosurgical generator The present disclosure provides an electrosurgical generator adapted to supply electrosurgical energy to tissue. The electrosurgical generator includes a power source is configured to deliver power to one or more types of loads connected to the electrosurgical generator. The electrosurgical generator includes a controller including a microprocessor coupled to the electro surgical generator and configured to control the output of the electrosurgical generator. A fiber optic connection circuit is in operative communication with the controller and includes one or more types of logic devices and one or more types of fiber optic channels. The fiber optic connection circuit is configured to mitigate leakage current associated with at least one of a plurality of components operatively associated with the electrosurgical generator by providing isolation.

BRIEF DESCRIPTION OF THE DRAWING

Various embodiments of the present disclosure are described hereinbelow with references to the drawings, wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

As noted above, leakage current associated with RF generators may be problem in some instances. To reduce and/or mitigate leakage currents typically associated with RF generators, the generator of the present disclosure employs a fiber optic connection circuit that is operatively associated with a low voltage power supply of the generator. More particularly, the fiber optic connection circuit provides a primary fiber optic isolation barrier at a RF amp output module associated with a high voltage power supply side of the generator and on the low voltage power supply side of the generator.

Figure 1A:
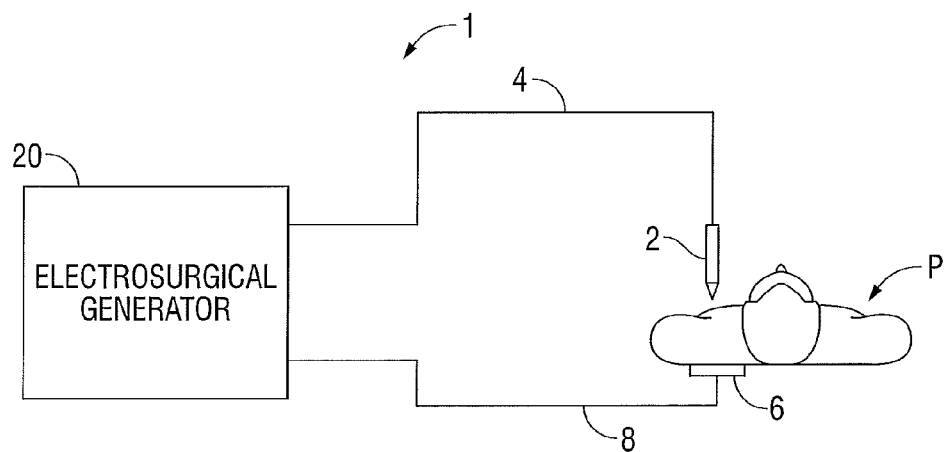
FIG. 1A is a schematic block diagram of a monopolar electrosurgical system in accordance with an embodiment of the present disclosure.

FIG. 1A is a schematic illustration of a monopolar electrosurgical system 1 configured for use with a generator 20 according to one embodiment of the present disclosure. The system 1 includes a monopolar electrosurgical instrument 2 having one or more electrodes for treating tissue of a patient P (e.g., electrosurgical cutting, ablation, etc.). More particularly, electrosurgical RF energy is supplied to the instrument 2 by the generator 20 via a supply line 4 that is connected to an active terminal 34 (FIG. 2) of the generator 20, allowing the instrument 2 to coagulate, ablate and/or otherwise treat tissue. The energy is returned to the generator 20 through a return electrode 6 via a return line 8 at a return terminal 36 (FIG. 2) of the generator 20. The active terminal 34 and the return terminal 36 are connectors configured to interface with plugs (not explicitly shown) of the instrument 2 and the return electrode 6, which are disposed at the ends of the supply line 4 and the return line 8, respectively.

Figure 1B:
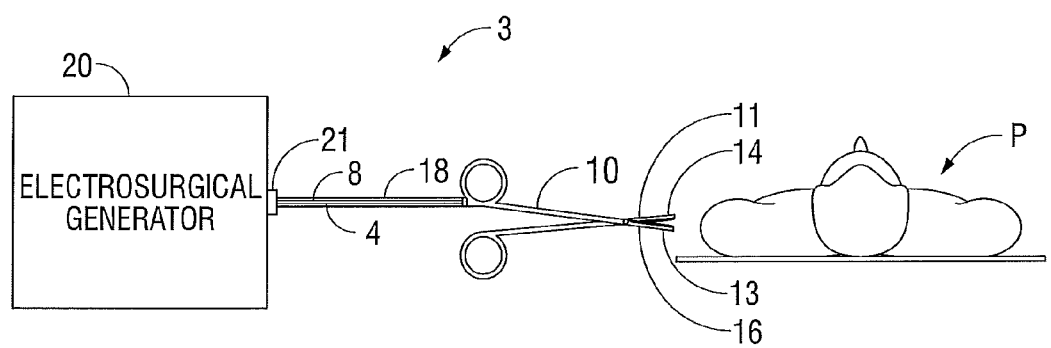
FIG. 1B is a schematic block diagram of a bipolar electrosurgical system in accordance with another embodiment of the present disclosure.
Figure 2:
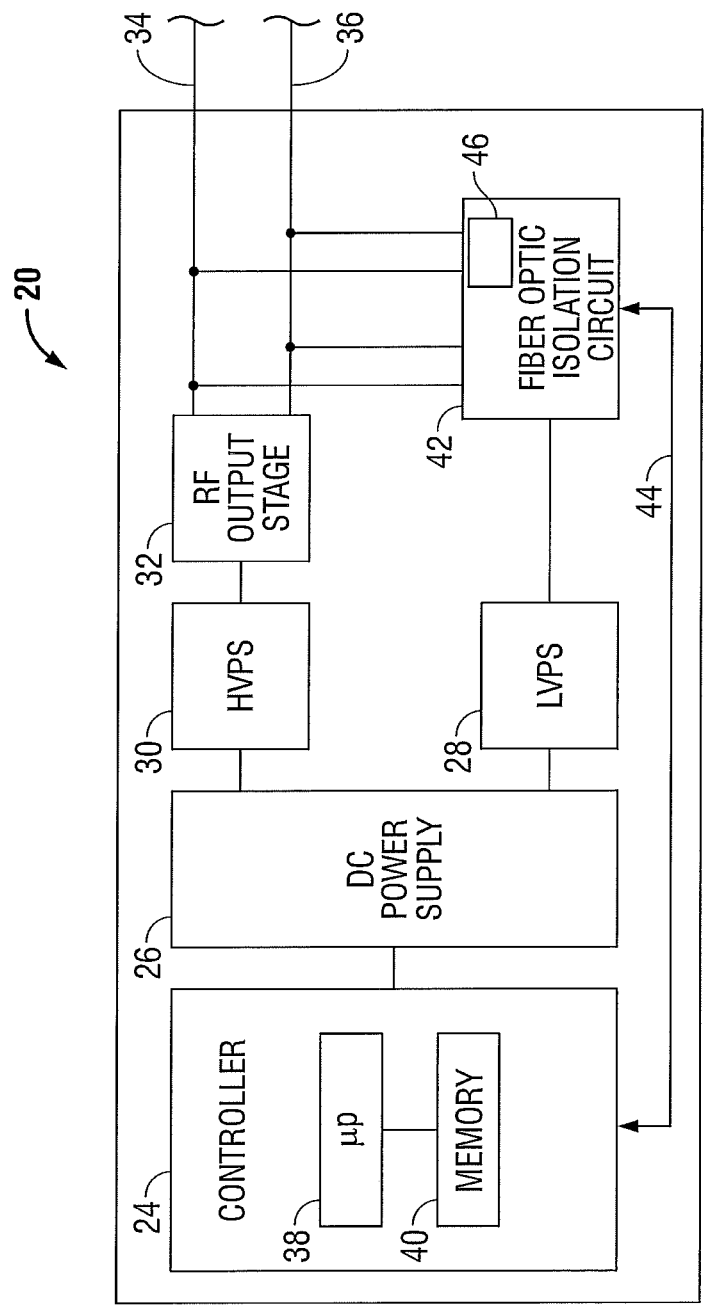
FIG. 2 is a schematic block diagram of a generator in accordance with an embodiment of the present disclosure.

FIG. 1B is a schematic illustration of a bipolar electrosurgical system 3 configured for use with the generator 20 according to the present disclosure. The system 3 includes a bipolar electrosurgical forceps 10 having one or more electrodes for treating tissue of a patient P. The electrosurgical forceps 10 includes opposing jaw members 11 and 13 having an active electrode 14 and a return electrode 16, respectively, disposed therein. The active electrode 14 and the return electrode 16 are connected to the generator 20 through cable 18, which includes supply and return lines 4, 8 coupled to the active and return terminals 34, 36, respectively (FIG. 2). The electrosurgical forceps 10 is coupled to the generator 20 at a connector 21 having connections to the active and return terminals 34 and 36 (e.g., pins) plug disposed at the end of the cable 18. The connector 21 includes contacts from the supply and return lines 4, 8.

While the drawings depict an electrosurgical forceps 10 that is suitable for use in performing an open electrosurgical procedure, it is within the purview of the present disclosure that other types of electrosurgical forceps, e.g., electrosurgical forceps suitable for use in performing a endoscopic electrosurgical procedure, may be employed with the generator 20.

The generator 20 includes suitable input controls (e.g., buttons, activators, switches, touch screen, etc.) for controlling the generator 20. In addition, the generator 20 may include one or more display screens for providing a user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.).

FIG. 2 shows a schematic block diagram of the generator 20 having a controller 24 and DC power supply 26. The DC power supply 26 is connected to a conventional AC source (e.g., electrical wall outlet) and includes a low voltage power supply 28 ("LVPS") and a high voltage power supply 30 ("HVPS"). The HVPS 30 provides high voltage DC power to an RF output stage 32, e.g., an RF amp module 32, which then converts high voltage DC power into RF energy and delivers the RF energy to the active terminal 34. The energy is returned thereto via the return terminal 36. The LVPS 29 provides power to various components of the generator (e.g., input controls, displays, etc.), as will be discussed in further detail below. Each of the HVPS and LVPS may include one or more DC-DC converters 68 configured to increase or decrease the power supplied by the DC power supply 26. In embodiments, the generator 20 may include one or more power factor connection (PFC) modules 64 serving as boost regulators and in operative communication with each of the HVPS and LVPS. The PFC module 64 serves to improve the power factor of the generator 20 and regulate the incoming line voltage to a constant. With this purpose in mind, the PFC module 64 may include any number of capacitors, contactors, and/or inductors The generator 20 may include a plurality of connectors to accommodate various types of electrosurgical instruments (e.g., electrosurgical surgical instrument 2, electrosurgical forceps 10, etc.). Further, the generator 20 may be configured to operate in a variety of modes such as ablation, monopolar and bipolar cutting, coagulation, etc. The generator 20 may also include a switching mechanism (e.g., relays) to switch the supply of RF energy between the connectors, such that, for example, when the instrument 2 is connected to the generator 20, only the monopolar plug receives RF energy.

The controller 24 includes a microprocessor 38 operably connected to a memory 40, which may be volatile type memory (e.g., RAM) and/or non-volatile type memory (e.g., flash media, disk media, etc.). The microprocessor 38 includes an output port that is operably connected to the DC power supply 26 and/or RF output stage 32 allowing the microprocessor 38 to control the output of the generator 20 according to either open and/or closed control loop schemes. Those skilled in the art will appreciate that the microprocessor 38 may be substituted by any logic processor (e.g., control circuit) adapted to perform the calculations discussed herein.

Figure 3:
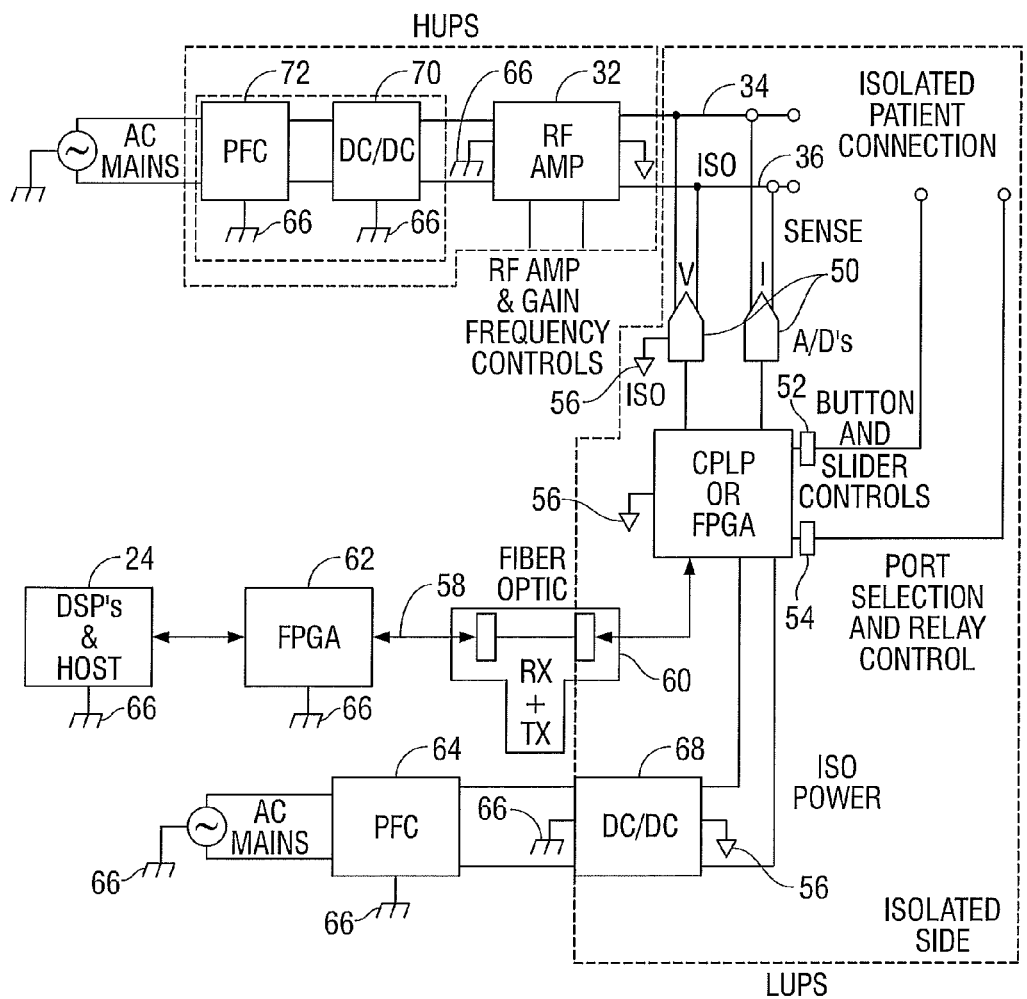
FIG. 3 is a schematic block diagram of specific components of the generator of FIG. 2.

With reference to FIGS. 2 and 3, a fiber optic connection circuit 42 (connection circuit 42) is configured to reduce or mitigate leakage current associated with one or more components (e.g., voltage and/or current sensors, buttons and/or slider controls, port selection and/or relay controls) associated with the generator 20. With this purpose in mind, the connection circuit 42 is powered by the LVPS and is in operative communication with the controller 24. The connection circuit 42 includes one or more fiber optic channels 44 and one or more logic devices 46.

Logic device 46 may be any suitable logic device. In the embodiment illustrated in FIG. 3, the logic device 46 a programmable array logic (PAL) device. In embodiments, the PAL device may be selected from the group consisting of a complex programmable logic device (CPLD) and a field programmable gate array (FPGA) device. In certain embodiments, the logic device 46 may include a combination of the CPLD and FPGA device. The specific configuration logic device 46 may vary based on the ultimate needs of a user. For example, the FPGA device may be employed when a high degree of accuracy is required in monitoring and/or measuring the power output of the generator 20. In an embodiment, the FPGA may include a processor core. Conversely, the CPLD may be employed when a high degree of accuracy is not required in monitoring and/or measuring the power output of the generator 20.

Logic device 46 is powered by the DC power supply 26 via a DC-DC converter 68 that is operatively disposed on the LVPS side of the generator 20. Logic device 46 may be in operative communication with one or more components associated with the LVPS 28. More particularly, one or more of the pins associated with the logic device 46 connects to one or more voltage and current sensors 50, button and slider controls 52 and/or port selection and relay controls 54 of the generator 20 (FIG. 3). A pin of the logic device 46 is connected to a signal ground 56. Each of the voltage and current sensors connects to the active and return terminals 34 and 36, respectively.

Fiber optic channel 44 provides a bi-directional data link to the controller 24. The fiber optic channel 44 may be based on any suitable data link protocol including but not limited to Ethernet, R5232/422/485, Sony/Philips Digital Interconnect Format (more commonly known as S/PDIF), etc. In the embodiment illustrated in FIG. 3 the fiber optic channel 44 is in the form of an Ethernet cable 58 and provides a data link between the logic device 46 and the controller 24. In the embodiment illustrated in FIG. 3, a second FPGA 62 that is coupled to chassis ground 66 is operatively associated with the controller 24 and serves as an intermediate interface between the controller 24 and fiber optic channel 44. In an embodiment, the second FPGA 62 may include a processor core (e.g., a digital signal processor, "DSP"), or may be replaced by a CPLD. One or more transmit and receive buffers (collectively referred to as buffers 60) is used to regulate the flow of data frames between the microprocessor 39 and logic array 46. As can be appreciated by one skilled in the art, increasing the number of buffers 60 between the logic device 46 and the second FPGA 62, microprocessor 38 and/or controller 24 improves overall generator performance during periods of heavy data transmission traffic between the logic device 46 and the second FPGA 62, microprocessor 38 and/or controller 24.

In an embodiment, it may prove useful to isolate an input side of the RF amp module 32. In this instance, the HVPS 30 may include a DC-DC converter 70 that is operatively connected to a PFC module serving as a boost regulator (FIG. 3).

In use, the fiber optic connection circuit 42 provides an isolation barrier on the low voltage power supply side of the generator 20 and, more particularly, on a low voltage digital side associated with the generator 20. The fiber optic channel 44 of the fiber optic connection circuit 42 provides an ideal transmitting medium for either high or low voltage measurements. In addition, the fiber optic connection circuit 42 and integral components associated therewith are configured to provide electrical isolation from the HVPS, e.g., RF output stage and electromagnetic interference (EMI) associated therewith; this EMI may be present while the fiber optic connection circuit 42 is measuring and/or monitoring voltage and currents associated with one or more components of the generator 20. However, because of the dielectric nature of optical fibers, connection circuit 42 and integral components associated therewith are immune to the EMI. That is, since the optical fiber in the fiber optic channel 44 has no metallic components, the fiber optic channel 44 can be installed in areas with EMI, including radio frequency interference (RFI).

While several embodiments of the disclosure are shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   a power source configured to supply power to at least one load electrically coupled to the power source;
   a plurality of operative components configured to control operation of the power source; and
   a fiber optic connection circuit coupled to the power supply and configured to provide isolation between at least one of the plurality of operative components and the power source and to mitigate leakage current associated with at least one of the plurality of operative components.

2. The electrosurgical generator according to claim 1, wherein the fiber optic connection circuit includes at least one logic device.

3. The electrosurgical generator according to claim 1, wherein the fiber optic connection circuit includes at least one fiber optic channel.

4. The electrosurgical generator according to claim 1, wherein at least one of the plurality of operative components includes an activation device selected from the group consisting of a switch, voltage divider network, a potentiometer, and combinations thereof.

5. The electrosurgical generator according to claim 1, wherein at least one of the plurality of operative components includes at least one of a port selector or a relay controller.

6. The electrosurgical generator according to claim 1, wherein at least one of the plurality of operative components includes at least one of a voltage sensor or current sensor.

7. The electrosurgical generator according to claim 6, wherein each of the voltage sensor and current sensor is connected to the power source.

8. An electrosurgical generator comprising:
   a power source configured to supply power to at least one load electrically coupled to the power source;
   a plurality of operative components configured to control operation of the power source; and
   a fiber optic connection circuit coupled to the power supply and configured to provide isolation between at least one of the plurality of operative components and the power source and to mitigate leakage current associated with at least one of the plurality of operative components, the fiber optic connection circuit including at least one logic device and at least one fiber optic channel.

9. The electrosurgical generator according to claim 8, wherein at least one of the plurality of operative components includes an activation device selected from the group consisting of a switch, voltage divider network, a potentiometer, and combinations thereof.

10. The electrosurgical generator according to claim 8, wherein at least one of the plurality of operative components includes at least one of a port selector or a relay controller.

11. The electrosurgical generator according to claim 8, wherein at least one of the plurality of operative components includes at least one of a voltage sensor or current sensor.

12. The electrosurgical generator according to claim 11, wherein each of the voltage sensor and current sensor is connected to the power source.

\* \* \* \* \*